United States Patent [19]
Mittal et al.

[11] Patent Number: 5,716,385
[45] Date of Patent: Feb. 10, 1998

[54] CRURAL DIAPHRAGM PACEMAKER AND METHOD FOR TREATING ESOPHAGEAL REFLUX DISEASE

[75] Inventors: Ravinder K. Mittal, Chiville; Robert Ross, Charlottesville; Jiamnim Liu, Charlottesville; Bruce Schirmer, Charlottesville, all of Va.

[73] Assignee: University of Virginia, Charlottesville, Va.

[21] Appl. No.: 747,513

[22] Filed: Nov. 12, 1996

[51] Int. Cl.⁶ ............................................. A61N 1/36
[52] U.S. Cl. ........................................................ 607/40
[58] Field of Search ............................. 607/2, 40, 41; 128/898

[56] References Cited

U.S. PATENT DOCUMENTS

| | | |
|---|---|---|
| 3,236,240 | 2/1966 | Bradley .................... 607/40 |
| 4,271,827 | 6/1981 | Angelchik ................ 128/898 |
| 5,292,344 | 3/1994 | Douglas ..................... 607/40 |
| 5,423,872 | 6/1995 | Cigaina ...................... 607/40 |

*Primary Examiner*—Marvin M. Lateef
*Assistant Examiner*—Kennedy J. Schaetzle
*Attorney, Agent, or Firm*—Whitham, Curtis, Whitham & McGinn

[57] ABSTRACT

An electronic pacemaker is used to counter-act crural diaphragm relaxation thereby preventing and/or treating gastroesophageal reflux. The pacemaker can be implantable, or be connected to the skeletal muscles of the crural diaphragm through the skin. A sensor is used to identify spontaneous intermittent relaxations of the diaphragm. During these spontaneous intermittent relaxations, one or more electrodes are used to stimulate the skeletal muscles of the crural diaphragm to cause contraction of the lower esophageal sphincter.

17 Claims, 2 Drawing Sheets

CRURAL DIAPHRAGM PACEMAKER AND METHOD FOR TREATING ESOPHAGEAL REFLUX DISEASE

BACKGROUND OF THE INVENTION

1. Field of the Invention

The invention is related to therapeutic gastroenterology and, more particularly, to an electrical stimulating device and method used to pace the crural diaphragm.

2. Description of the Prior Art

Gastroesophageal reflux is commonly treated using pharmaceuticals or by surgical procedures. In the pharmaceutical approach, the disease is treated most efficiently using H2 receptor antagonists and proton pump inhibitors. This class of drug is widely used in the U.S. and throughout the world, and sales of these products are believed to total more than $20,000,000,000 annually. The major disadvantage of pharmaceutical therapy is that it is a suppressive therapy and does not treat the cause of the disease. Thus, the pharmaceuticals must be consumed every day for the entire life of the patient. Surgical treatment is typically performed only when the symptoms and situation are fairly advanced, and poses the problems inherent in any major operation.

U.S. Pat. No. 5,423,872 to Cigeina describes pacing of the stomach to alter its natural rhythm. The principle espoused in Cigeina is that by altering the rhythm, one can either delay or speed up gastric emptying. Cigeina indicates that many different disorders including reflux disorders can be treated using the rhythm altering methodology. Cigeina suggests that reflux disorders can be treated by using the electrical stimulator during a digestive rest phase to promote sphincter release. However, the Cigeina device is not likely to be effective for treating such disorders because it contemplates stimulating smooth muscles, and electrical stimulation of the smooth muscles of the lower esophageal sphincter will result in relaxation of the sphincter rather than contraction.

U.S. Pat. No. 5,292,344 to Douglas discloses a percutaneously placed electrical gastrointestinal pacemaker which provide for both sensing and electrical pacing of the stomach. Like Cigeina, Douglas contemplates pacing the smooth muscle of the lower esophageal sphincter or stomach. Furthermore, Douglas is primarily directed to the treatment of stomach arrhythmias, not reflux disorders.

SUMMARY OF THE INVENTION

It is an object of this invention to provide a crural diaphragm pacemaker.

It is another object of this invention to provide a method of treating gastroesophageal reflux disease by selectively applying electrical stimulation to the skeletal muscles of the crural diaphragm.

According to the invention, electrical pacing is used to override crural diaphragm inhibition during intermittent or transient lower esophageal sphincter relaxations (TLESR), and thereby treat gastroesophageal reflux. An implantable or external electrical pacemaker is connected to electrode(s) positioned on the crural diaphragm. When crural diaphgram inhibition is sensed during TLESR, the crural diaphragm is electrically stimulated.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
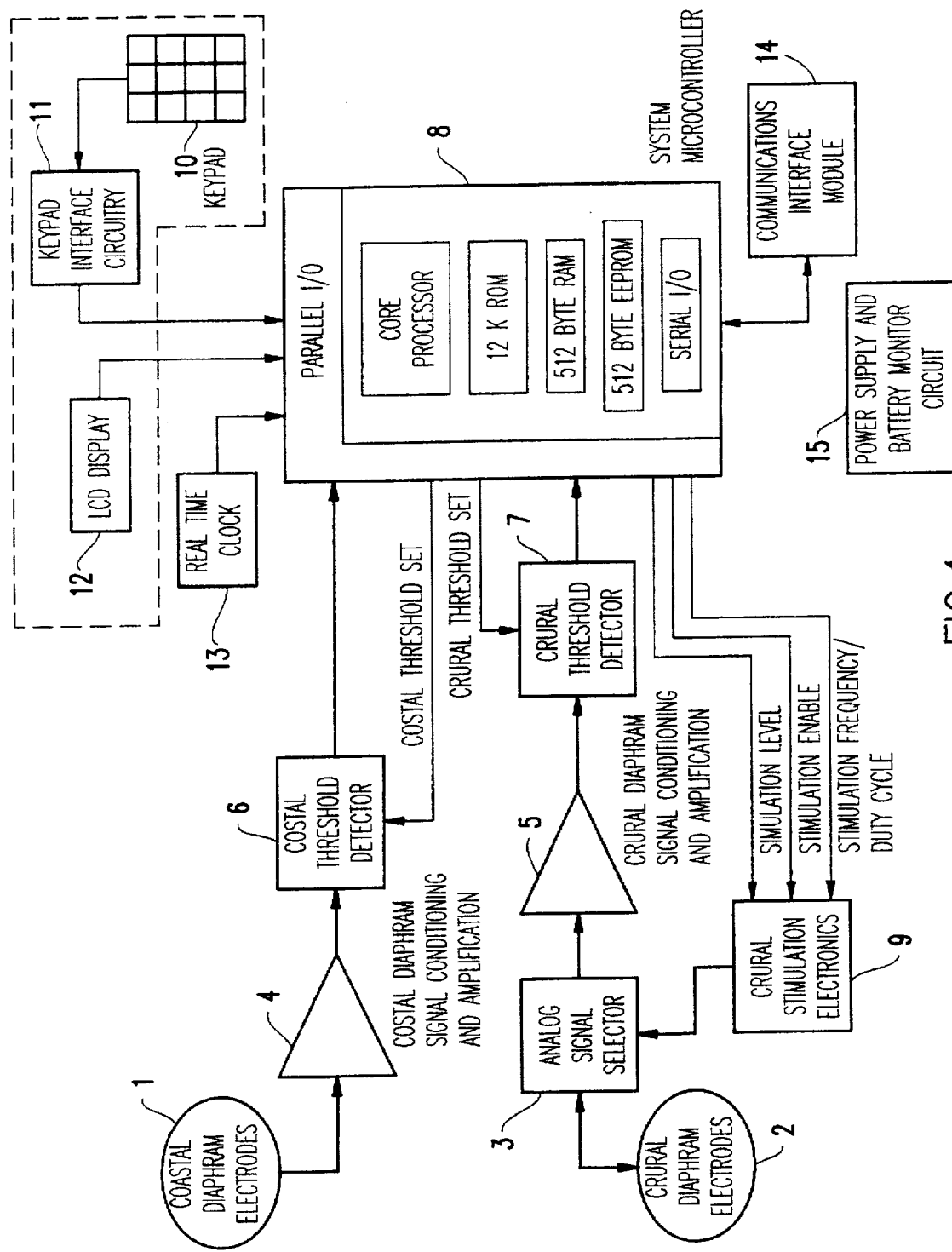
FIG. 1 is a schematic diagram of the electrical pacemaker of the present invention.
Figure 2A:
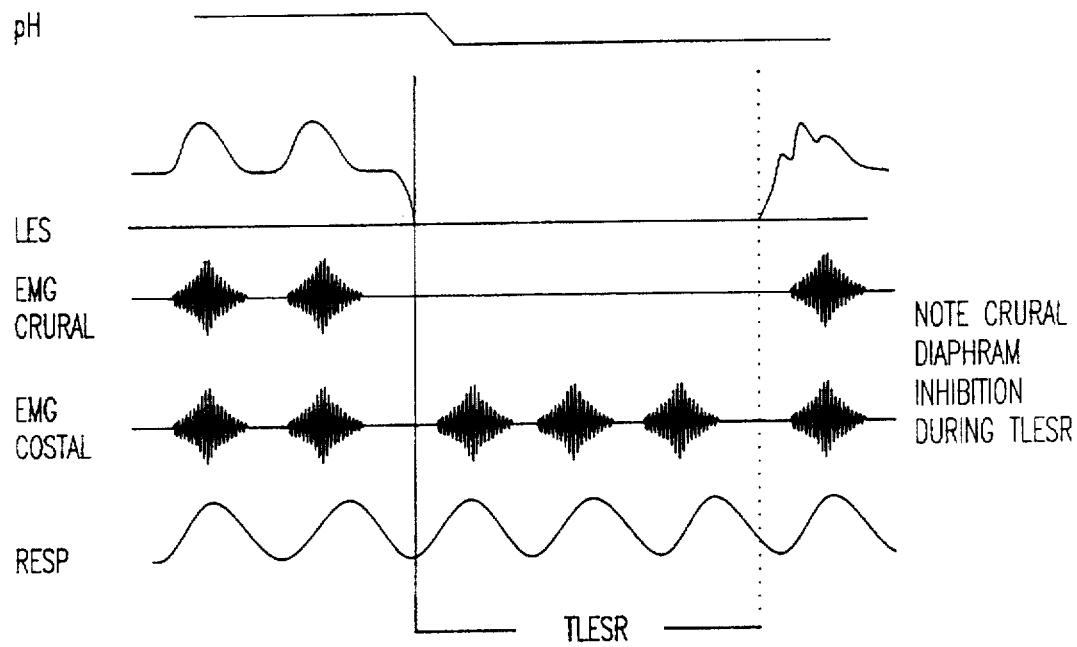
FIGS. 2a and 2b are line graphs illustrating electrical pacing in the prevention of reflux.
Figure 2B:
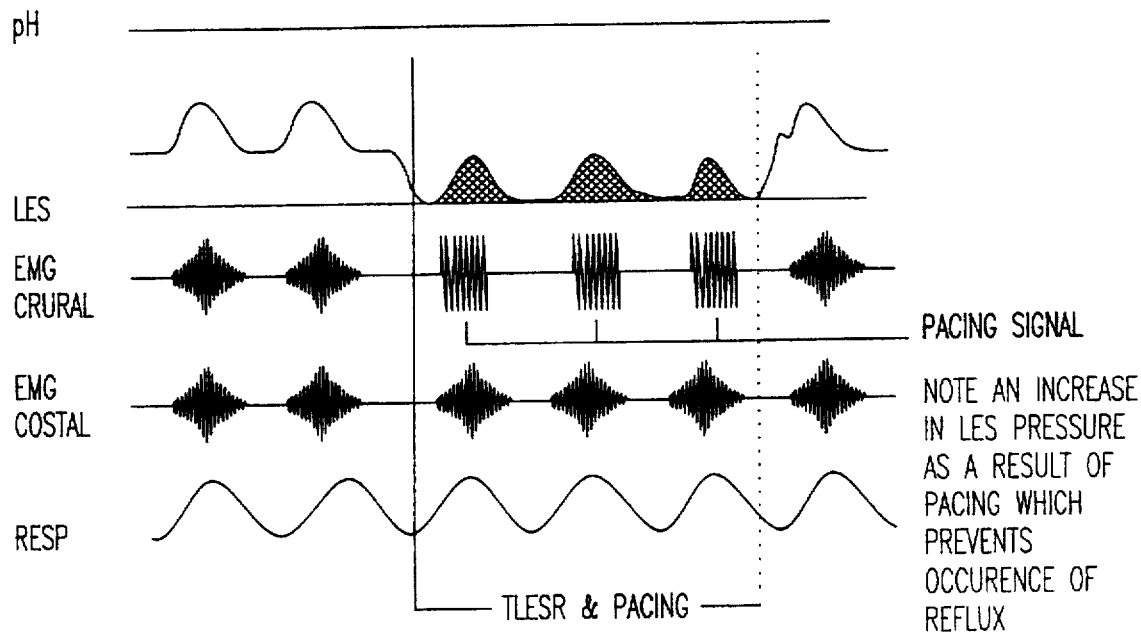

FIG. 1 shows an example of an electrical pacemaker designed for pacing the crural diaphragm according to the present invention. FIGS. 2a–b illustrate the pacing concept of this invention in the prevention of gastroesophageal reflux. It should be understood by those of skill in the art that the components used in the pacemaker as well as the mode of operation discussed below in connection with FIG. 1 could be varied considerably within the scope of the claimed invention. In addition, while the major role of the pacemaker is to treat esophagus reflux disease as explained in conjunction with FIGS. 2a–b, the pacemaker may also be useful in the treatment of achalasia and other esophageal motor disorders that are related to dysfunction of the crural diaphragm With reference to FIG. 1, myoelectric signals are received from by electrode pairs 1 and 2 placed on the patient's costal and crural diaphragm muscle tissue, respectively. These electrodes may be composed of or be plated with platinum, iridium, or other suitable materials. The costal diaphragm electrodes 1 and crural diaphragm electrodes 2 will be implanted surgically through a small incision in the patient's abdomen, either through a laparascopy or an open approach. Once the electrodes are positioned, the wires connected to the electrodes 1 and 2 will be tunneled under the skin. In the case of an external pacemaker unit which may be ideal for temporary use, the wires will be connected to a pacemaker that is preferably worn by the patient using a belt placed around the abdomen or chest. In the case of a permanent implantable device, the pacemaker will ideally be implanted under the skin of the abdominal wall. The pacemaker has the following functions:

A) It will sense and/or record electromyography signals from the crural and costal diaphragm simultaneously.

B) It will analyze the electromyography signals and will determine whether there is an inhibition of the crural diaphragm signal in the absence of an inhibition of the costal diaphragm. That is, the pacemaker will sense selective inhibition in the crural diaphragm which takes place during periods of spontaneous TLESR.

C) After sensing inhibition, the pacemaker will provide electrical stimulation to the crural diaphragm to electrically pace the muscles of the crural diaphragm and thereby override the inhibition.

It has been determined that spontaneous TLESR is the key mechanism of gastroesophageal reflux. The concept of selective crural diaphragm inhibition during TLESR has been observed in humans and animals. Studies in animals have demonstrated that electrical stimulation of the crural diaphragm increases the lower esophageal pressure.

With reference to FIG. 2a, it can be seen that during spontaneous TLESR and acid reflux, the patient's respiratory activity and the activity of the patient's costal diaphragm (as indicated by the repetitive Electromyogram (EMG) signal) remain unchanged. However, activity of the crural diaphragm is inhibited, the lower esophageal sphincter pressure drops and the pH in the esophagus decreases and becomes more acidic.

With reference to FIG. 2b, it can be seen that, according to this invention, by electrically pacing the crural diaphragm during the TLESR period with an intermittent pacing signal, the lower esophageal sphincter pressure is increased, and this increase in pressure results in preventing the occurrence of reflux as indicated by the steady pH signal. Thus, this invention contemplates sensing inhibition of the crural diaphragm during TLESR, and pacing the crural diaphragm to increase lower esophageal sphincter pressure and thereby prevent or reduce reflux. The preferred embodiment of the invention is to monitor both the costal and crural diaphragms of the patient and to begin pacing when the crural diaphragm is inhibited while the costal diaphragm is not inhibited. Pacing would preferably be at the same frequency as the costal diaphragm contraction and would end when the crural diaphragm resumes normal functions. The optimum pacing frequency for each patient can vary and might be "learned" by monitoring the particular patient's crural diaphragm contractions and deducing the optimum frequency from these sensed signals. In addition, pacing might simply be performed each time crural diaphragm inhibition is detected.

With reference back to FIG. 1, crural diaphragm myoelectric signals pass through an analog signal selector 3 before further processing. The analog signal selector 3 allows the crural diaphragm electrodes 2 to be used for monitoring crural diaphragm myoelectric signals as well as for electrical stimulation of the crural diaphragm muscle tissue during TSLER. Alternatively, different electrodes could be used for sensing and stimulation. Costal and crural diaphragm signal conditioning and amplification circuits 4 and 5, respectively, provide appropriate band-pass filtering and amplification of costal and crural myoelectric signals with significant attenuation of caridac, electrical stimulation and other electrical artifacts. Costal and crural diaphragm signal threshold detectors 6 and 7, respectively, accept processed signals from costal and crural diaphragm signal conditioning and amplification circuits 4 and 5, and detect the presence of a costal or crural diaphragm contraction when the incoming signal amplitude exceeds a voltage threshold set by the pacemaker microcomputer 8.

The pacemaker microcomputer 8 preferably is a single chip microcomputer system such as a Motorola® MC68HC711 or Microchip PIC device with on-board core processor, random access memory (RAM), read only memory (ROM), electrically erasable programmable read only memory (EEPROM) for non-volatile storage of pacing parameters and status and serial/parallel input/output devices (I/O).

Crural diaphragm stimulation electronics 9 provide signal stimulation to the patient's crural diaphragm muscle tissue during TLESK by passing an electrical signal to the crural diaphragm electrodes 2 through the device's analog signal selector 3. The stimulation signal produced by the crural stimulation electronics 9 preferably takes the form of a constant current square wave with frequency between 40 and 400 hertz with a duty cycle of 10–50%. The pacemaker's stimulation level is preferably adjustable between 100 microamperes and 10 milliamperes. The duration of a crural diaphragm stimulation cycle is preferably adjustable between 1.5 and 2.5 seconds. As shown in FIG. 1, the pacemaker microcrontroller 8 should be connected to the crural diaphragm electronics 9 and be capable of setting stimulation frequency, duty cycle, duration and stimulation level through software control.

As discussed above, the pacemaker has two preferred embodiments. The first embodiment is a portable, Walkman® sized, battery operated device worn external to the patient's body. Costal and crural diaphragm electrical connections would be achieved using transcutaneous electrodes.

The second preferred embodiment would be an implantable design that would be used for long-term treatment on a permanent or semi-permanent basis. Both embodiments would preferably operate as "on-demand" units. That is, as discussed above, electrical pacing would be implemented only when crural diaphragm inhibition exists. No pacing would occur when the crural diaphragm is not inhibited.

An externally worn pacemaker would preferably have a number of I/O devices allowing the physician to set pacing parameters and monitor pacing status. For example, FIG. 1 shows a keypad device 10 which keypad interface circuitry 11 which allows the physician to program pacemaker parameters such as stimulation frequency/duty cycle, stimulation level, stimulation duration, costal and crural detector thresholds and costal/crural diaphragm contraction delay time. These parameters would be stored in the pacemaker's microcontroller 8 non-volatile EEPROM memory. FIG. 1 also shows a liquid crystal display (LCD) used by the physician or patient to monitor pacing status or verify previously stored pacing parameters. One particular use of the LCD 12 and keypad 10 would be for the physician to initiate a timed study where it is important to know the exact number of crural diaphragm stimulation cycles the device has administered to the patient in a twenty four hour period. To begin the study, the physician would enter a command through keypad 10 upon which time the real time clock time keeping element 13 would begin a twenty four hour countdown. During that twenty four hour period, the pacemaker's microcontroller 8 would accumulate and record crural diaphragm stimulation cycles. At the end of the study, the total number of crural diaphragm stimulation cycles administered to the patient within the previous twenty four hour period would be indicated on the LCD 12.

Communications module 14 would allow the crural diaphragm pacemaker to communicate with a personal computer or other similar device. Similar to the keypad 10 and LCD 12 functions, a personal computer could be used to program pacing parameters and monitor pacing status. In the case of an externally worn pacemaker, communications interface 14 could be an RS-232C type serial interface for connection to the serial port of a personal computer. This connection to an external personal computer can be optically isolated in order to ensure against electrical hazard to the patient.

An implantable crural diaphragm pacemaker would not include keypad 10, keypad interface circuitry 11 or LCD display 12. All communications with the implantable pacemaker would be through communications interface module 14 which in this case would take the form of a transcutaneous wireless transceiver. This wireless interface would be used for programming and monitoring pacing parameters and status, and possibly for recharging the implantable pacemaker's batter power source.

Both external and implantable pacemakers should have a power supply and battery monitor circuit 15 which would be used to alert the patient or physician of a low battery power situation. In the case of an external pacemaker, this warning could be communicated to the patient or physician through the LCD 12 or RS-232C type communications module 14. In the case of an implantable pacemaker, a low battery warning would be communicated to the physician through the transcutaneous wireless communications module 14. In either case, low battery status should be stored in the system microcontroller's 8 non-volatile EEPROM memory.

It is envisioned that certain alternate embodiments of the crural diaphragm pacemaker would involve modification of the technique used by the device to detect the presence of a costal or crural diaphragm contraction. One alternative implementation would used digital signal processing (DSP) techniques wherein costal and crural diaphragm signal threshold detectors 6 and 7 would each be replaced by a system composed of an analog-to-digital conversion (ADC) followed by a DSP processor. The ADC would sample the analog signals produced by costal and crural diaphragm signal conditioning and amplification circuits 4 and 5, respectively, and convert these analog samples into digital data. This digital information would then be passed to a DSP processor which would be able to identify the presence of a costal or crural diaphragm contraction, by processing the data through fast fourier transform (FFT) or digital filtering algorithms. The DSP processor used for this application could be a Texas Instruments® TMS320C40 or other similar device. In another alternative embodiment, the crural diaphragm pacemaker would employ the use of back propagation electronic neural networks as a replacement for costal and crural diaphragm signal detectors 6 and 7. Back propagating neural networks have the ability to identify or "learn" the unique electrical signature of a costal or crural diaphragm contraction after being conditioned or "trained" by costal and crural diaphragm myoelectric signals over a period of time.

While the invention has been described in terms of its preferred embodiments, those skilled in the art will recognize that the invention can be practiced with modification within the spirit and scope of the appended claims.

We claim:

1. A crural diaphragm pacemaker, comprising:
   means for sensing crural diaphragm inhibition; and
   means for providing electrical stimulation to a patient's crural diaphragm.

2. The crural diaphragm pacemaker of claim 1 further comprising means for determining a time period when a patient is experiencing transient lower esophageal sphincter relaxation, said means for providing electrical stimulation being selectively activated during said time period.

3. The crural diaphragm pacemaker of claim 2 further comprising means for monitoring a patient's costal diaphragm.

4. The crural diaphragm pacemaker of claim 3 wherein said means for providing electrical stimulation includes a means for providing electrical stimuli to said patient's crural diaphragm at the same frequency as contractions of said patient's costal diaphragm sensed by said means for monitoring.

5. The crural diaphragm pacemaker of claim 1 wherein said means for providing electrical stimulation includes a means for providing electrical stimulus to said patient's crural diaphragm only when crural diaphragm inhibition is sensed.

6. The crural diaphragm pacemaker of claim 1 wherein said means for providing electrical stimulation includes a means for providing electrical stimulus to said patient's crural diaphragm on an intermittent basis.

7. A crural diaphragm pacemaker, comprising:
   a crural diaphragm electrode connectable to a patient's crural diaphragm; and
   a controller connected to said crural diaphragm electrode, said controller selectively directing said crural diaphragm electrode to provide electrical stimulation to a patient's crural diaphragm.

8. The crural diaphragm pacemaker of claim 7 further comprising costal diaphragm electrode connectable to a patient's costal diaphragm, said costal diaphragm electrode being connected to said controller and providing signals representative of a patient's costal diaphragm contractions.

9. The crural diaphragm pacemaker of claim 8 wherein said controller directs said crural diaphragm electrode to provide electrical stimulation to a patient's crural diaphragm at substantially the same frequency as a patient's costal diaphragm contractions sensed with said costal diaphragm electrode.

10. The crural diaphragm pacemaker of claim 7 wherein said crural diaphragm electrode functions to both sense inhibition of a patient's crural diaphragm and provide electrical stimulation to a patient's crural diaphragm.

11. The crural diaphragm pacemaker of claim 7 further comprises a means for programming said controller to adjust any one of the parameters selected from the group consisting of stimulation level, stimulation frequency, enablement of stimulation, and duty cycle.

12. The crural diaphragm pacemaker of claim 7 further comprising a communications interface module which communicates with said controller.

13. A method for treating gastroesophageal reflux, comprising the steps of:
   sensing spontaneous intermittent relaxations of a patient's crural diaphragm; and
   providing sufficient electrical stimulation to said patient's crural diaphragm to cause contraction of said patient's lower esophageal sphincter.

14. The method of claim 13 wherein said step of providing electrical stimulation is performed intermittently.

15. A method of electrically pacing a patient's crural diaphragm, comprising the steps of:
   detecting crural diaphragm inhibition for said patient; and
   electrically stimulating said patient's crural diaphragm when crural diaphragm inhibition is detected during said detecting step.

16. The method of claim 15 further comprising the step of detecting said patient's costal diaphragm contractions, said step of electrically stimulating being performed when said patient's crural diaphragm is inhibited and said patient's costal diaphragm is functioning normally.

17. The method of claim 16 wherein said step of electrically stimulating is performed at the same frequency as said patient's crural diaphragm contractions.

* * * * *